United States Patent
Jiang et al.

(10) Patent No.: US 12,116,615 B2
(45) Date of Patent: Oct. 15, 2024

(54) STABILIZER FOR COLOR DEVELOPING AGENT AND APPLICATION THEREOF, APPLICATION OF COMPOSITION IN PREPARATION OF STABILIZER, AND KIT

(71) Applicant: DA AN GENE CO., LTD., Guangdong (CN)

(72) Inventors: Xiwen Jiang, Guangdong (CN); Wenchuang Qi, Guangdong (CN); Runfeng Wu, Guangdong (CN); Junxing Jian, Guangdong (CN); Chuanfei Mo, Guangdong (CN); Yizhu Yin, Guangdong (CN); Suwei Lei, Guangdong (CN)

(73) Assignee: DA AN GENE CO., LTD., Guangdong (CN)

( * ) Notice: Subject to any disclaimer, the term of this patent is extended or adjusted under 35 U.S.C. 154(b) by 0 days.

(21) Appl. No.: 18/024,502

(22) PCT Filed: May 17, 2022

(86) PCT No.: PCT/CN2022/093389
§ 371 (c)(1),
(2) Date: Mar. 3, 2023

(87) PCT Pub. No.: WO2023/206640
PCT Pub. Date: Nov. 2, 2023

(65) Prior Publication Data
US 2023/0340561 A1   Oct. 26, 2023

(30) Foreign Application Priority Data

Apr. 26, 2022   (CN) .......................... 202210447077.8

(51) Int. Cl.
C12Q 1/28   (2006.01)
B01L 3/00   (2006.01)

(52) U.S. Cl.
CPC .............. *C12Q 1/28* (2013.01); *B01L 3/5023* (2013.01); *B01L 2200/16* (2013.01); *B01L 2300/069* (2013.01); *G01N 2333/902* (2013.01)

(58) Field of Classification Search
None
See application file for complete search history.

(56) References Cited

U.S. PATENT DOCUMENTS

2008/0241816 A1   10/2008   Taniguchi et al.

FOREIGN PATENT DOCUMENTS

| CN | 103884833 | | 6/2014 |
| CN | 114875115 | | 8/2022 |
| JP | H06289015 | | 10/1994 |
| JP | H08202003 | | 8/1996 |
| JP | 2007055233 | | 3/2007 |
| JP | 2009160937 | | 7/2009 |
| JP | 2011120599 | A * | 6/2011 |
| JP | 2019176802 | A * | 10/2019 |

OTHER PUBLICATIONS

UNL ("Buffer pKa and pH Range Values", University of Nebraska, Lincoln Nebraska, available at https://animalscience.unl.edu/Research/RumNut/RumNutLab/99-bufferpkaandphrangevalues%281%29.pdf, accessed on Jul. 19, 2023). (Year: 2023).*
"International Search Report (Form PCT/ISA/210) of PCT/CN2022/093389," mailed on Nov. 28, 2022, pp. 1-5.
"Written Opinion of the International Searching Authority (Form PCT/ISA/237) of PCT/CN2022/093389," mailed on Nov. 28, 2022, with English translation thereof, pp. 1-6.

* cited by examiner

*Primary Examiner* — Robert J Yamasaki
*Assistant Examiner* — Charles Zoltan Constantine
(74) *Attorney, Agent, or Firm* — JCIPRNET (57) ABSTRACT

Disclosed in the present invention are a stabilizer for a color developing agent and application thereof, an application of a composition in preparation of the stabilizer, and a kit. A stabilizer for a color developing agent is provided in the present invention. The stabilizer includes a reducing substance and a weakly acidic buffer, and the weakly acidic buffer has a pH of 3.8-6.2. The reducing substance includes one or more of sodium sulfite, sodium bisulfite, sodium thiosulfate, or 1-mercaptoglycerol. The color developing agent includes one or two of a phenothiazine color developing agent or a triphenylmethane color developing agent. The color developing agent can be stably preserved by using the stabilizer. A method for stably preserving a color developing agent includes dissolving the color developing agent in the stabilizer.

3 Claims, 3 Drawing Sheets

STABILIZER FOR COLOR DEVELOPING AGENT AND APPLICATION THEREOF, APPLICATION OF COMPOSITION IN PREPARATION OF STABILIZER, AND KIT

CROSS-REFERENCE TO RELATED APPLICATION

This application is a 371 of international application of PCT application serial no. PCT/CN2022/093389, filed on May 17, 2022, which claims the priority benefit of China application no. 202210447077.8, filed on Apr. 26, 2022. The entirety of each of the above mentioned patent applications is hereby incorporated by reference herein and made a part of this specification.

BACKGROUND

Technical Field

The present invention belongs to the field of chemical detection, and specifically relates to a stabilizer and a stabilizing method for a color developing agent.

Description of Related Art

Changes of various components in various body fluids of the human body are closely related to the occurrence of diseases. When risk prediction and auxiliary diagnosis of the diseases and determination of therapeutic monitoring are carried out, the changes of some components in the body fluids, such as glycosylated hemoglobin, glycosylated albumin, uric acid, urea, glucose, triglyceride, and other various trace components in the blood are usually subjected to qualitative and quantitative analysis. The qualitative and quantitative analysis of the trace components plays a great role in the auxiliary diagnosis of the diseases.

At present, many means are used for qualitative and quantitative analysis of the various trace components in the body fluids of the human body. An enzyme-coupled colorimetric method has been widely used in clinical determination. The method includes making a target component interact with oxidase with a specific effect to produce hydrogen peroxide, inducing the hydrogen peroxide into a color developing system by using peroxidase (POD) and an oxidized color developing agent as a color developing component, and then obtaining the amount of the target component based on a color developing degree obtained by colorimetric quantification. As a well-known color developing system, a Trinder reagent includes 4-aminoantipyrine (4-AAP) or 3-methyl-2-benzothiazole hydrazone (MBTH) which undergoes oxidation condensation with a phenol derivative, an aniline derivative and other chromophores to produce a pigment. However, the color developing system including an oxidized color developing agent has low sensitivity in quantitative analysis of the trace components, and is likely to be affected by hemoglobin and bilirubin in a sample. In order to solve the problems of the typical Trinder reagent, a novel hydrogen peroxide color developing reagent has been widely concerned. However, due to low stability of the novel hydrogen peroxide color developing agent, the problem of easy spontaneous color development is caused, so that the application of the novel hydrogen peroxide color developing agent is limited.

A stabilizer for a color developing agent and application thereof are disclosed in the prior art. The stabilizer can be used for well stabilizing a color developing agent, such as 3,3',5,5'-tetramethylbenzidine (TMB). However, the stabilizer contains an azo dye, which will increase the overall blank of the reagent, so that practical application is not facilitated. Therefore, a novel stabilizing method and a stabilizer for a color developing agent are required to be developed.

SUMMARY

Technical problems to be solved by the present invention are to overcome the defects of existing stabilizing methods for hydrogen peroxide color developing agents and to provide a stabilizer and a stabilizing method for a color developing agent.

An objective of the present invention is to provide a stabilizer for a color developing agent.

Another objective of the present invention is to provide application of a composition in preparation of a stabilizer for a color developing agent.

Another objective of the present invention is to provide application of the stabilizer in detection by an enzyme-coupled colorimetric method or in preparation of a kit for detection by an enzyme-coupled colorimetric method.

Another objective of the present invention is to provide a stabilizing method for a color developing agent.

Another objective of the present invention is to provide a kit.

The above objectives of the present invention are realized by adopting the following technical means.

A stabilizer for a color developing agent is provided. The stabilizer includes a reducing substance and a weakly acidic buffer, and the weakly acidic buffer has a pH of 3.8-6.2. The reducing substance includes one or more of sodium sulfite, sodium bisulfite, sodium thiosulfate and 1-mercaptoglycerol. The color developing agent includes one or two of a phenothiazine color developing agent and a triphenylmethane color developing agent.

Preferably, the weakly acidic buffer has a pH of 4-6.

Further preferably, the weakly acidic buffer has a pH of 5.

Preferably, the reducing substance includes one or two of the sodium sulfite and the sodium thiosulfate.

Further preferably, when the color developing agent is the phenothiazine color developing agent, the reducing substance is the sodium thiosulfate. When the color developing agent is the triphenylmethane color developing agent, the reducing substance is the sodium sulfite.

Further preferably, when the color developing agent is the phenothiazine color developing agent, the weakly acidic buffer has a pH of 5-6, and the reducing substance is the sodium thiosulfate. When the color developing agent is the triphenylmethane color developing agent, the weakly acidic buffer has a pH of 4-5, and the reducing substance is the sodium sulfite.

Preferably, the reducing substance has a concentration of 0.01-20 mM.

Further preferably, the reducing substance has a concentration of 1-10 mM.

Further preferably, the reducing substance has a concentration of 10 mM.

Further preferably, when the color developing agent is the phenothiazine color developing agent, the weakly acidic buffer has a pH of 5, and the reducing substance is the sodium thiosulfate with a concentration of 10 mM. When the color developing agent is the triphenylmethane color developing agent, the weakly acidic buffer has a pH of 5, and the reducing substance is the sodium sulfite with a concentration of 10 mM.

Preferably, the weakly acidic buffer includes one or more of a citric acid buffer, a phosphate buffer, a 4-morpholinoethanesulfonic acid buffer (MES buffer), an acetic acid buffer and an imidazole buffer.

Further preferably, the weakly acidic buffer includes one or two of the citric acid buffer and the 4-morpholinoethanesulfonic acid buffer (MES buffer).

Preferably, the phenothiazine color developing agent includes one or two of sodium 10-(carboxymethylaminocarbonyl)-3,7-bis(dimethylamino)phenothiazine (DA-67) and 3,7-bis(dimethylamino)-N-ethyl-10H-phenothiazine-10-formamide (MCDP).

Preferably, the triphenylmethane color developing agent includes one or two of leucomalachite green and leucocrystal violet.

Application of a composition in preparation of a stabilizer for a color developing agent is provided. The composition is the stabilizer for a color developing agent. The stabilizer includes a reducing substance and a weakly acidic buffer. The color developing agent includes one or two of a phenothiazine color developing agent an a triphenylmethane color developing agent.

Application of the stabilizer in detection by an enzyme-coupled colorimetric method or in preparation of a kit for detection by an enzyme-coupled colorimetric method also falls within the protection scope of the present invention.

A kit includes a reagent R2. The reagent R2 includes the color developing agent and the stabilizer. The kit is used for detection by an enzyme-coupled colorimetric method.

Preferably, the color developing agent includes a phenothiazine color developing agent or a triphenylmethane color developing agent.

The kit further includes a reagent R1. The reagent R1 includes one or more of a buffer, peroxidase, a preservative, oxidase, synthase and adenosine triphosphate (ATP).

Preferably, the kit further includes a pre-treatment solution. The pre-treatment solution includes a surfactant and sodium nitrite.

Further preferably, the surfactant is Triton X-100, Twin-20, or Triton X-405.

Further preferably, the surfactant is the Triton X-100.

Preferably, the oxidase in the reagent R1 is fructosyl-amino acid oxidase or acyl-coenzyme A oxidase.

Preferably, the synthase in the reagent R1 is acyl-coenzyme A synthase.

Preferably, the reagent R2 includes a buffer stabilizer which contains sodium thiosulfate and has a pH of 5-6, and a phenothiazine color developing agent.

Further preferably, the reagent R2 includes a buffer stabilizer which contains sodium thiosulfate and has a pH of 5, and a phenothiazine color developing agent.

Preferably, the reagent R2 includes a buffer stabilizer which contains sodium sulfite and has a pH of 4-5, and a triphenylmethane color developing agent.

Further preferably, the reagent R2 includes a buffer stabilizer which contains sodium sulfite and has a pH of 5, and a triphenylmethane color developing agent.

Preferably, the reagent R2 further includes a preservative, a surfactant, and a coenzyme A.

Preferably, the preservative is Proclin-300 or sodium benzoate.

Preferably, the surfactant is straight-chain secondary alcohol polyoxyethylene ether (Tergitol™ 15-S-9) or Genapol X 080.

Further preferably, the surfactant is the straight-chain secondary alcohol polyoxyethylene ether (Tergitol™ 15-S-9).

As a specific embodiment, a kit is used for detecting glycosylated hemoglobin in a blood sample by an enzyme-coupled colorimetric method. The kit includes a pre-treatment solution, a reagent R1, and a reagent R2. The pre-treatment solution includes Triton X-100 and sodium nitrite. The reagent R1 includes a Tris-HCl buffer, peroxidase, fructosyl-amino acid oxidase, and sodium azide. The reagent R2 includes 4-morpholinoethanesulfonic acid buffer (MES buffer), sodium 10-(carboxymethylaminocarbonyl)-3,7-bis(dimethylamino)phenothiazine (DA-67), sodium thiosulfate, and Proclin-300.

A method of using the kit for detecting glycosylated hemoglobin in a blood sample includes: adding an anticoagulant, namely disodium EDTA, to a whole blood sample for centrifugation and layering; taking red blood cells from the lowest layer for thorough mixing with the pre-treatment solution to obtain a pre-treatment sample; uniformly mixing the pre-treatment sample with the reagent R1 for incubation at 37° C. for 5 minutes, and determining an absorbance A1; and then, adding the reagent R2 for uniform mixing and incubation at 37° C. for 5 minutes, and determining an absorbance A2.

As a specific embodiment, a kit is used for detecting a free fatty acid in a blood sample by an enzyme-coupled colorimetric method. The kit includes a reagent R1 and a reagent R2. The reagent R1 includes a HEPES buffer, acyl-coenzyme A synthase, acyl-coenzyme A oxidase, ATP, peroxidase, and sodium azide. The reagent R2 includes a citric acid buffer, straight-chain secondary alcohol polyoxyethylene ether (Tergitol™ 15-S-9), a coenzyme A, leucomalachite green, sodium sulfite, and sodium benzoate.

A method of using the kit for detecting a free fatty acid in a blood sample includes: uniformly mixing serum with the reagent R2 for incubation at 37° C. for 5 minutes, and determining an absorbance A1 at a wavelength of 600 nm; and then, adding 45 μL of the reagent R1 for uniform mixing and incubation at 37° C. for 5 minutes, and determining an absorbance A2 at a wavelength of 600 nm.

A stabilizing method for a color developing agent is provided. When the color developing agent is dissolved in the stabilizer, spontaneous color development of the color developing agent can be suppressed, and the color developing agent is stably preserved.

The stabilizer includes a reducing substance and a weakly acidic buffer, and the weakly acidic buffer has a pH of 3.8-6.2. The reducing substance includes one or more of sodium sulfite, sodium bisulfite, sodium thiosulfate and 1-mercaptoglycerol. The color developing agent includes one or two of a phenothiazine color developing agent and a triphenylmethane color developing agent.

According to the present invention, when the color developing agent is preserved by using the stabilizer containing a reducing substance, the spontaneous color development of the color developing agent can be suppressed, while properties and application of the color developing agent are not affected.

Compared with the prior art, the present invention has the following beneficial effects.

(1) According to the present invention, the phenothiazine color developing agent or the triphenylmethane color developing agent is preserved by using the weakly acidic buffer or the weakly acidic buffer containing a reducing substance as a stabilizer, so that the spontaneous color development of the color developing agent can be suppressed, the time for preservation of the color developing agent is prolonged, and the color developing ability of the color developing agent is maintained. Meanwhile, a redox reaction of the color developing agent is not interfered, and the stabilizer can be used in stable preservation of the phenothiazine color developing agent or the triphenylmethane color developing agent.

(2) The color developing agent can be stably preserved by using the stabilizer. A method for stably preserving a color developing agent includes dissolving the color developing agent in the stabilizer. The color developing agent can be stably preserved in the stabilizer for 2 weeks, and the stabilizer does not have a suppression effect on the color developing agent in subsequent use. Not only the problems of low stability and easy spontaneous color development of the color developing agent are solved, but also influence of the stabilizer on properties of the color developing agent is avoided, thereby a novel method is provided for preservation of the color developing agent.

DESCRIPTION OF THE EMBODIMENTS

The present invention is further described in conjunction with specific embodiments, but the embodiments are not intended to limit the present invention in any form. Unless otherwise specified, reagents, methods, and devices used in the present invention are conventional reagents, methods, and devices in the technical field.

Unless otherwise specified, reagents and materials used in the following embodiments are commercially available.

A preservation solution mentioned in the present invention is the stabilizer.

A Tris buffer (with a pH of 8.00) is obtained by dissolving 1.21 g trihydroxymethylaminomethane in 50 mL purified water, adjusting the pH to 8.00 with hydrochloric acid, and then adding purified water to reach a volume of 100 mL.

A phosphate buffer (with a pH of 7.00) is obtained by dissolving 1.20 g anhydrous sodium dihydrogen phosphate in 50 mL purified water, adjusting the pH to 7.00 with sodium hydroxide, and then adding purified water to reach a volume of 100 mL.

An MES buffer (with a pH of 6.00) is obtained by dissolving 1.95 g 2-(N-morpholine)ethanesulfonic acid in 50 mL purified water, adjusting the pH to 6.00 with sodium hydroxide, and then adding purified water to reach a volume of 100 mL.

An imidazole buffer (with a pH of 6.00) is obtained by dissolving 0.68 g trihydroxymethylaminomethane in 50 mL purified water, adjusting the pH to 6.00 with hydrochloric acid, and then adding purified water to reach a volume of 100 mL.

A citric acid buffer (with a pH of 5.00) is obtained by dissolving 2.10 g citric acid monohydrate in 50 mL purified water, adjusting the pH to 5.00 with sodium hydroxide, and then adding purified water to reach a volume of 100 mL.

An MES buffer (with a pH of 5.00) is obtained by dissolving 1.95 g 2-(N-morpholine)ethanesulfonic acid in 50 mL purified water, adjusting the pH to 5.00 with sodium hydroxide, and then adding purified water to reach a volume of 100 mL.

An acetic acid buffer (with a pH of 4.00) is obtained by dissolving 1.36 g sodium acetate trihydrate in 50 mL purified water, adjusting the pH to 4.00 with hydrochloric acid, and then adding purified water to reach a volume of 100 mL.

A potassium hydrogen phthalate buffer (with a pH of 4.00) is obtained by dissolving 2.04 g potassium hydrogen phthalate in 50 mL purified water, adjusting the pH to 4.00 with sodium hydroxide, and then adding purified water to reach a volume of 100 mL.

Example 1 Stability of DA-67 Under Different Buffer Preservation Conditions

1. Method

A color developing agent, namely sodium 10-(carboxymethylaminocarbonyl)-3,7-bis(dimethylamino)phenothiazine (DA-67), was dissolved in different buffer preservation solutions separately, where the color developing agent DA-67 had a final concentration of 50 µM. The solutions were preserved at 37° C. for 2 weeks. Parts of the solutions were extracted every 2 days. The absorbance at a wavelength of 660 nm was determined by an ultraviolet spectrophotometer.

2. Results

Changes of the absorbance of the color developing agent DA-67 under different preservation conditions including numbers 1-8 are as shown in Table 1.

TABLE 1

Changes of the absorbance of the color developing agent DA-67 under different preservation conditions including numbers 1-8

| | Absorbance Number | | | | | | | |
|---|---|---|---|---|---|---|---|---|
| | 1 | 2 | 3 | 4 | 5 | 6 | 7 | 8 |
| | Preservation solution | | | | | | | |
| Number of days | 100 mM Tris-HCl buffer pH = 8.00 | 100 mM phosphate buffer pH = 7.00 | 100 mM MES buffer pH = 6.00 | 100 mM imidazole buffer pH = 6.00 | 100 mM citric acid buffer pH = 5.00 | 100 mM MES buffer pH = 5.00 | 100 mM acetic acid buffer pH = 4.00 | 100 mM potassium hydrogen phthalate buffer pH = 4.00 |
| 0 day | 0.0313 | 0.0308 | 0.0322 | 0.0331 | 0.0318 | 0.0314 | 0.0330 | 0.0330 |
| 2nd day | 0.2877 | 0.2704 | 0.3420 | 0.3522 | 0.1988 | 0.1988 | 0.2100 | 0.2100 |
| 4th day | 0.5435 | 0.4717 | 0.3891 | 0.4007 | 0.3315 | 0.3248 | 0.3886 | 0.3886 |

TABLE 1-continued

Changes of the absorbance of the color developing agent DA-67 under different preservation conditions including numbers 1-8

| | Absorbance Number | | | | | | | |
|---|---|---|---|---|---|---|---|---|
| | 1 | 2 | 3 | 4 | 5 | 6 | 7 | 8 |
| | Preservation solution | | | | | | | |
| Number of days | 100 mM Tris-HCl buffer pH = 8.00 | 100 mM phosphate buffer pH = 7.00 | 100 mM MES buffer pH = 6.00 | 100 mM imidazole buffer pH = 6.00 | 100 mM citric acid buffer pH = 5.00 | 100 mM MES buffer pH = 5.00 | 100 mM acetic acid buffer pH = 4.00 | 100 mM potassium hydrogen phthalate buffer pH = 4.00 |
| 6th day | 0.7938 | 0.7001 | 0.5921 | 0.5980 | 0.5342 | 0.5502 | 0.5850 | 0.5850 |
| 8th day | 1.0517 | 0.9223 | 0.7719 | 0.7796 | 0.6520 | 0.6454 | 0.7382 | 0.7382 |
| 10th day | 1.3049 | 1.1496 | 0.9225 | 0.9317 | 0.8925 | 0.9014 | 0.9395 | 0.9395 |
| 12th day | 1.5559 | 1.2898 | 1.1062 | 1.0951 | 0.9413 | 0.8942 | 1.1015 | 1.1015 |
| 14th day | 1.8105 | 1.5678 | 1.2800 | 1.2672 | 1.2166 | 1.2287 | 1.2963 | 1.2963 |
| Difference of the absorbance between the 14th day and the 0 day | 1.7792 | 1.537 | 1.2478 | 1.2341 | 1.1848 | 1.1973 | 1.2633 | 1.2633 |

From Table 1, it can be seen that the color developing agent DA-67 preserved in different buffer preservation solutions at 37° C. for 2 weeks has significant difference in absorbance. With the increase of preservation days, the color developing agent DA-67 has a basically same change trend. The absorbance of the DA-67 in a 100 mM Tris-HCl buffer with a pH of 8.00 is increased by 1.7792. The absorbance of the DA-67 in a 100 mM phosphate buffer with a pH of 7 is increased by 1.537. However, the absorbance in a buffer with a pH of 4-6 is only increased by 1.1848-1.2633, and the absorbance in a buffer with a pH of 5.00 is only increased by 1.1848 or 1.1973, which is the smallest change in absorbance. It is indicated that the change of the absorbance of the DA-67 in a slightly acidic environment (such as a buffer with a pH of 4-6) is significantly lower than that in a slightly alkaline environment. Compared with an alkaline buffer, a weakly acidic buffer preservation solution with a pH of 4-6 can significantly slow down spontaneous color development of the color developing agent, the spontaneous color development of the color developing agent is suppressed to a certain extent, and the color developing agent is stabilized. A weakly acidic buffer preservation solution with a pH of 5 has the best effect of suppressing the spontaneous color development of the color developing agent.

Example 2 Stability of DA-67 Under Different Reducing Substance Preservation Conditions 1. Method A color developing agent, namely sodium 10-(carboxymethylaminocarbonyl)-3,7-bis(dimethylamino)phenothiazine (DA-67), was dissolved in different reducing substance preservation solutions separately, where the color developing agent DA-67 had a final concentration of 50 μM. The solutions were preserved at 37° C. for 2 weeks. Parts of the solutions were extracted every 2 days. The absorbance at a wavelength of 660 nm was determined by an ultraviolet spectrophotometer.

2. Results

Changes of the absorbance of the color developing agent DA-67 under different preservation conditions including numbers 9-12 are as shown in Table 2.

TABLE 2

Changes of the absorbance of the color developing agent DA-67 under different preservation conditions including numbers 9-12

| | Absorbance Number | | | |
|---|---|---|---|---|
| | 9 | 10 | 11 | 12 |
| | Preservation solution | | | |
| | 100 mM citric acid buffer with a pH of 5.00 | | | |
| Number of days | 3 mM sodium sulfite | 3 mM sodium thiosulfate | 3 mM sodium bisulfite | 3 mM 1-mercaptoglycerol |
| 0 day | 0.0288 | 0.0246 | 0.0267 | 0.0258 |
| 2nd day | 0.1444 | 0.1227 | 0.1173 | 0.1165 |
| 4th day | 0.3027 | 0.2208 | 0.2608 | 0.2407 |
| 6th day | 0.4048 | 0.3190 | 0.3278 | 0.3921 |
| 8th day | 0.5931 | 0.4172 | 0.5121 | 0.5016 |
| 10th day | 0.6550 | 0.5153 | 0.6446 | 0.5676 |
| 12th day | 0.8464 | 0.6137 | 0.6674 | 0.6534 |
| 14th day | 0.9143 | 0.7119 | 0.8219 | 0.7821 |
| Difference of the absorbance between the 14th day and the 0 day | 0.8855 | 0.6873 | 0.7952 | 0.7563 |

From Table 2, it can be seen that the color developing agent DA-67 preserved in different reducing substance preservation solutions at 37° C. for 2 weeks has a basically same change trend in absorbance. In different reducing substance preservation solutions, the absorbance of the DA-67 in a citric acid buffer preservation solution which has a pH of 5 and contains 3 mM sodium thiosulfate is only increased by 0.6873, which is the smallest change in absorbance, and the solution has a better effect of suppressing spontaneous color development than other reducing substances such as sodium sulfite, sodium bisulfite, and 1-mercaptoglycerol.

When the preservation solution is changed into other buffer solutions with a pH of 5, a preservation solution containing sodium thiosulfate also has a better effect of suppressing spontaneous color development than other reducing substances such as sodium sulfite, sodium bisulfite, and 1-mercaptoglycerol.

Example 3 Stability of DA-67 Under Different Concentrations of Sodium Thiosulfate Preservation Conditions 1. Method A color developing agent, namely sodium 10-(carboxymethylaminocarbonyl)-3,7-bis(dimethylamino)phenothiazine (DA-67), was dissolved in different concentrations of sodium thiosulfate preservation solutions separately, where the color developing agent DA-67 had a final concentration of 50 μM. The solutions were preserved at 37° C. for 2 weeks. Parts of the solutions were extracted every 2 days. The absorbance at a wavelength of 660 nm was determined by an ultraviolet spectrophotometer.

2. Results

Changes of the absorbance of the color developing agent DA-67 under different preservation conditions including numbers 13-16 are as shown in Table 3.

TABLE 3

Changes of the absorbance of the color developing agent DA-67 under different preservation conditions including numbers 13-16

| | Absorbance Number | | | |
|---|---|---|---|---|
| | 13 | 14 | 15 | 16 |
| | Preservation solution | | | |
| | 100 mM citric acid buffer with a pH of 5.00 | | | |
| Number of days | 1 mM sodium thiosulfate | 5 mM sodium thiosulfate | 7 mM sodium thiosulfate | 10 mM sodium thiosulfate |
| 0 day | 0.026 | 0.0218 | 0.0225 | 0.0235 |
| 2nd day | 0.1298 | 0.1072 | 0.0979 | 0.0807 |
| 4th day | 0.2408 | 0.1925 | 0.1664 | 0.1391 |
| 6th day | 0.3419 | 0.2845 | 0.2705 | 0.1977 |
| 8th day | 0.4426 | 0.36 | 0.3158 | 0.2766 |
| 10th day | 0.5606 | 0.4586 | 0.4343 | 0.3267 |
| 12th day | 0.6542 | 0.5639 | 0.5179 | 0.3719 |
| 14th day | 0.7731 | 0.6378 | 0.5374 | 0.4477 |
| Difference of the absorbance between the 14th day and the 0 day | 0.7471 | 0.616 | 0.5149 | 0.4242 |

From Table 3, it can be seen that the color developing agent DA-67 preserved in different concentrations of sodium thiosulfate preservation solutions at 37° C. for 2 weeks has a basically same change trend in absorbance. In different concentrations of sodium thiosulfate preservation solutions, the absorbance of the DA-67 in a citric acid buffer preservation solution which has a pH of 5 and contains 10 mM sodium thiosulfate is only increased by 0.4242, which is the smallest change in absorbance, and the solution has the best effect of suppressing spontaneous color development. It can be seen that when the DA-67 is preserved in the citric acid buffer which has a pH of 5 and contains 10 mM sodium thiosulfate, an optimal stabilizing effect is achieved.

When the preservation solution is changed into other buffer solutions with a pH of 5, a buffer containing 10 mM sodium thiosulfate also has an optimal effect of stabilizing the DA-67.

Example 4 Stability of Leucomalachite Green Under Different Buffer Preservation Conditions 1. Method A color developing agent, namely leucomalachite green, was dissolved in different buffer preservation solutions separately, where the color developing agent leucomalachite green had a final concentration of 10 μM. The solutions were preserved at 37° C. for 2 weeks. Parts of the solutions were extracted every 2 days. The absorbance at a wavelength of 660 nm was determined by an ultraviolet spectrophotometer.

2. Results

Changes of the absorbance of the color developing agent leucomalachite green under different preservation conditions including numbers 17-24 are as shown in Table 4.

TABLE 4

Changes of the absorbance of the color developing agent leucomalachite green under different preservation conditions including numbers 17-24

| | Absorbance Number | | | | | | | |
|---|---|---|---|---|---|---|---|---|
| | 17 | 18 | 19 | 20 | 21 | 22 | 23 | 24 |
| | Preservation solution | | | | | | | |
| Number of days | 100 mM Tris-HCl buffer pH = 8.00 | 100 mM phosphate buffer pH = 7.00 | 100 mM MES buffer pH = 6.00 | 100 mM imidazole buffer pH = 6.00 | 100 mM citric acid buffer pH = 5.00 | 100 mM MES buffer pH = 5.00 | 100 mM acetic acid buffer pH = 4.00 | 100 mM Potassium hydrogen phthalate buffer pH = 4.00 |
| 0 day | 0.0088 | 0.0080 | 0.0091 | 0.0095 | 0.0089 | 0.0086 | 0.0091 | 0.0091 |
| 2nd day | 0.0449 | 0.0414 | 0.0347 | 0.0347 | 0.0270 | 0.0280 | 0.0296 | 0.0287 |
| 4th day | 0.1237 | 0.1149 | 0.0974 | 0.0964 | 0.0759 | 0.0759 | 0.0828 | 0.0836 |

TABLE 4-continued

Changes of the absorbance of the color developing agent leucomalachite green under different preservation conditions including numbers 17-24

| | Absorbance Number | | | | | | | |
|---|---|---|---|---|---|---|---|---|
| | 17 | 18 | 19 | 20 | 21 | 22 | 23 | 24 |
| | Preservation solution | | | | | | | |
| Number of days | 100 mM Tris-HCl buffer pH = 8.00 | 100 mM phosphate buffer pH = 7.00 | 100 mM MES buffer pH = 6.00 | 100 mM imidazole buffer pH = 6.00 | 100 mM citric acid buffer pH = 5.00 | 100 mM MES buffer pH = 5.00 | 100 mM acetic acid buffer pH = 4.00 | 100 mM Potassium hydrogen phthalate buffer pH = 4.00 |
| 6th day | 0.1721 | 0.1600 | 0.1421 | 0.1421 | 0.1029 | 0.0987 | 0.1080 | 0.1069 |
| 8th day | 0.2365 | 0.2204 | 0.1757 | 0.1669 | 0.1430 | 0.1487 | 0.1594 | 0.1514 |
| 10th day | 0.3104 | 0.2812 | 0.2284 | 0.2375 | 0.1881 | 0.1824 | 0.2088 | 0.2171 |
| 12th day | 0.3555 | 0.3373 | 0.2636 | 0.2583 | 0.2182 | 0.2094 | 0.2374 | 0.2350 |
| 14th day | 0.3831 | 0.3589 | 0.2881 | 0.2823 | 0.2329 | 0.2375 | 0.2566 | 0.2617 |
| Difference of the absorbance between the 14th day and the 0 day | 0.3743 | 0.3509 | 0.2790 | 0.2728 | 0.2240 | 0.2289 | 0.2475 | 0.2526 |

From Table 4, it can be seen that the color developing agent leucomalachite green preserved in different buffer preservation solutions at 37° C. for 2 weeks has significant difference in absorbance. With the increase of preservation days, the absorbance of the leucomalachite green in a Tris-HCl buffer with a pH of 8 is increased by 0.3743. The absorbance in a phosphate buffer with a pH of 7.00 is increased by 0.3509. However, the absorbance in a buffer with a pH of 4-6 is only increased by 0.224-0.279, and the absorbance in a buffer with a pH of 5 is only increased by 0.224 or 0.2289, which is the smallest change in absorbance. It is indicated that the degree of spontaneous color development of the leucomalachite green under slightly acidic conditions (such as a buffer with a pH of 4-6) is lower than that under neutral or alkaline conditions. When the pH is 5, the effect of suppressing spontaneous color development is the best.

Example 5 Stability of Leucomalachite Green Under Different Reducing Substance Preservation Conditions 1. Method A color developing agent, namely leucomalachite green, was dissolved in different reducing substance preservation solutions separately, where the color developing agent leucomalachite green had a final concentration of 10 μM. The solutions were preserved at 37° C. for 2 weeks. Parts of the solutions were extracted every 2 days. The absorbance at a wavelength of 660 nm was determined by an ultraviolet spectrophotometer.

2. Results

Changes of the absorbance of the color developing agent leucomalachite green under different preservation conditions including numbers 25-28 are as shown in Table 5.

TABLE 5

Changes of the absorbance of the color developing agent leucomalachite green under different preservation conditions including numbers 25-28

| | Absorbance Number | | | |
|---|---|---|---|---|
| | 25 | 26 | 27 | 28 |
| | Preservation solution | | | |
| | 100 mM MES buffer with a pH of 5.00 | | | |
| Number of days | 3 mM sodium sulfite | 3 mM sodium thiosulfate | 3 mM sodium bisulfite | 3 mM 1-mercaptoglycerol |
| 0 day | 0.0087 | 0.0092 | 0.0084 | 0.0086 |
| 2nd day | 0.0232 | 0.0257 | 0.0261 | 0.0261 |
| 4th day | 0.0631 | 0.0721 | 0.0686 | 0.0727 |
| 6th day | 0.0843 | 0.0982 | 0.1008 | 0.0941 |
| 8th day | 0.1244 | 0.1401 | 0.1365 | 0.1341 |
| 10th day | 0.1653 | 0.1747 | 0.1803 | 0.1792 |
| 12th day | 0.1911 | 0.2055 | 0.2053 | 0.2022 |
| 14th day | 0.1912 | 0.2161 | 0.2105 | 0.2117 |
| Difference of the absorbance between the 14th day and the 0 day | 0.1825 | 0.2069 | 0.2021 | 0.2031 |

From Table 5, it can be seen that the color developing agent leucomalachite green preserved in different reducing substance preservation solutions at 37° C. for 2 weeks has significant difference in absorbance. With the increase of preservation days, the absorbance of the color developing agent leucomalachite green in an MES buffer which has a pH of 5 and contains 3 mM sodium sulfite is only increased by 0.1825, which is the smallest change in absorbance, and the buffer has a better effect of suppressing spontaneous color development than other reducing substances such as sodium thiosulfate, sodium bisulfite, and 1-mercaptoglycerol.

When the preservation solution is changed into other buffer solutions with a pH of 5, a preservation solution containing sodium sulfite also has a better effect of suppressing spontaneous color development than other reducing substances such as sodium thiosulfate, sodium bisulfite, and 1-mercaptoglycerol.

Example 6 Stability of Leucomalachite Green Under Different Concentrations of Sodium Sulfite Preservation Conditions 1. Method A color developing agent, namely leucomalachite green, was dissolved in different concentrations of sodium sulfite preservation solutions separately, where the color developing agent leucomalachite green had a final concentration of 10 μM. The solutions were preserved at 37° C. for 2 weeks. Parts of the solutions were extracted every 2 days. The absorbance at a wavelength of 660 nm was determined by an ultraviolet spectrophotometer.

2. Results

Changes of the absorbance of the color developing agent leucomalachite green under different preservation conditions including numbers 29-32 are as shown in Table 6.

TABLE 6

Changes of the absorbance of the color developing agent leucomalachite green under different preservation conditions including numbers 29-32

| | Absorbance Number | | | |
|---|---|---|---|---|
| | 29 | 30 | 31 | 32 |
| | Preservation solution | | | |
| | 100 mM MES buffer with a pH of 5.00 | | | |
| Number of days | 1 mM sodium sulfite | 5 mM sodium sulfite | 7 mM sodium sulfite | 10 mM sodium sulfite |
| 0 day | 0.0081 | 0.0086 | 0.0086 | 0.0083 |
| 2nd day | 0.0232 | 0.0202 | 0.0199 | 0.0162 |
| 4th day | 0.0631 | 0.0548 | 0.0567 | 0.0468 |
| 6th day | 0.0843 | 0.0725 | 0.0683 | 0.0627 |
| 8th day | 0.1244 | 0.1107 | 0.1007 | 0.0904 |
| 10th day | 0.1653 | 0.1472 | 0.1358 | 0.1165 |
| 12th day | 0.1911 | 0.1746 | 0.1612 | 0.1433 |
| 14th day | 0.1912 | 0.1682 | 0.1642 | 0.1412 |
| Difference of the absorbance between the 14th day and the 0 day | 0.1831 | 0.1596 | 0.1556 | 0.1329 |

From Table 6, it can be seen that the color developing agent leucomalachite green preserved in different concentrations of sodium sulfite preservation solutions at 3° C. for 2 weeks has significant difference in absorbance. With the increase of preservation days, the absorbance of the color developing agent leucomalachite green in an MES buffer which has a pH of 5 and contains 10 mM sodium sulfite is only increased by 0.1329, which is the smallest change in absorbance, and the buffer has an optimal effect of suppressing spontaneous color development. It can be seen that when the leucomalachite green is preserved in the MES buffer which has a pH of 5 and contains 10 mM sodium sulfite, an optimal stabilizing effect is achieved.

When the preservation solution is changed into other buffer solutions with a pH of 5, a buffer containing 10 mM sodium sulfite also has an optimal effect of stabilizing the leucomalachite green.

Example 7 Stability of Leucocrystal Violet Under Different Buffer Preservation Conditions 1. Method A color developing agent, namely leucocrystal violet, was dissolved in different buffer preservation solutions separately, where the color developing agent leucocrystal violet had a final concentration of 10 μM. The solutions were preserved at 37° C. for 2 weeks. Parts of the solutions were extracted every 2 days. The absorbance at a wavelength of 590 nm was determined by an ultraviolet spectrophotometer.

2. Results

Changes of the absorbance of the color developing agent leucocrystal violet under different preservation conditions including numbers 33-40 are as shown in Table 7.

TABLE 7

Changes of the absorbance of the color developing agent leucocrystal violet under different preservation conditions including numbers 33-40

| | Absorbance Number | | | | | | | |
|---|---|---|---|---|---|---|---|---|
| | 33 | 34 | 35 | 36 | 37 | 38 | 39 | 40 |
| | Preservation solution | | | | | | | |
| Number of days | 100 mM Tris-HCl buffer pH = 8.00 | 100 mM phosphate buffer pH = 7.00 | 100 mM imidazole buffer pH = 6.00 | 100 mM MES buffer pH = 6.00 | 100 mM MES buffer pH = 5.00 | 100 mM citric acid buffer pH = 5.00 | 100 mM acetic acid buffer pH = 4.00 | 100 mM potassium hydrogen phthalate buffer pH = 4.00 |
| 0 day | 0.0099 | 0.0093 | 0.0079 | 0.0082 | 0.0086 | 0.0087 | 0.0094 | 0.0093 |
| 2nd day | 0.0504 | 0.0458 | 0.0385 | 0.0365 | 0.032 | 0.0336 | 0.0337 | 0.0333 |
| 4th day | 0.1387 | 0.1264 | 0.1056 | 0.1034 | 0.09 | 0.0873 | 0.0936 | 0.0889 |

TABLE 7-continued

Changes of the absorbance of the color developing agent leucocrystal violet under different preservation conditions including numbers 33-40

| | Absorbance Number | | | | | | | |
|---|---|---|---|---|---|---|---|---|
| | 33 | 34 | 35 | 36 | 37 | 38 | 39 | 40 |
| | | | | Preservation solution | | | | |
| Number of days | 100 mM Tris-HCl buffer pH = 8.00 | 100 mM phosphate buffer pH = 7.00 | 100 mM imidazole buffer pH = 6.00 | 100 mM MES buffer pH = 6.00 | 100 mM MES buffer pH = 5.00 | 100 mM citric acid buffer pH = 5.00 | 100 mM acetic acid buffer pH = 4.00 | 100 mM potassium hydrogen phthalate buffer pH = 4.00 |
| 6th day | 0.1939 | 0.1772 | 0.151 | 0.1479 | 0.1215 | 0.1263 | 0.1316 | 0.1381 |
| 8th day | 0.2646 | 0.2391 | 0.2087 | 0.2170 | 0.1614 | 0.1565 | 0.1815 | 0.1905 |
| 10th day | 0.3476 | 0.3274 | 0.2756 | 0.2700 | 0.22 | 0.2090 | 0.236 | 0.2454 |
| 12th day | 0.4024 | 0.3802 | 0.3118 | 0.3086 | 0.2486 | 0.2535 | 0.2639 | 0.2691 |
| 14th day | 0.4329 | 0.3952 | 0.3298 | 0.3265 | 0.2614 | 0.2640 | 0.2818 | 0.2902 |
| Difference of the absorbance between the 14th day and the 0 day | 0.423 | 0.3859 | 0.3219 | 0.3183 | 0.2528 | 0.2553 | 0.2724 | 0.2809 |

From Table 7, it can be seen that the color developing agent leucocrystal violet preserved in different buffer preservation solutions at 37° C. for 2 weeks has significant difference in absorbance. With the increase of preservation days, the absorbance of the color developing agent leucocrystal violet in a Tris-HCl buffer with a pH of 8 is increased by 0.423. The absorbance in a phosphate buffer with a pH of 7.00 is increased by 0.3859. However, the absorbance in a buffer with a pH of 4-6 is only increased by 0.2528-0.3219, and the absorbance in a buffer with a pH of 5 is only increased by 0.2528 or 0.2553, which is the smallest change in absorbance. It is indicated that the degree of spontaneous color development of the leucocrystal violet under slightly acidic conditions (such as a buffer with a pH of 4-6) is lower than that under neutral or alkaline conditions. When the pH is 5, the effect of suppressing spontaneous color development is the best.

Example 8 Stability of Leucocrystal Violet Under Different Reducing Substance Preservation Conditions 1. Method A color developing agent, namely leucocrystal violet, was dissolved in different reducing substance preservation solutions separately, where the color developing agent leucocrystal violet had a final concentration of 10 μM. The solutions were preserved at 37° C. for 2 weeks. Parts of the solutions were extracted every 2 days. The absorbance at a wavelength of 590 nm was determined by an ultraviolet spectrophotometer.

2. Results

Changes of the absorbance of the color developing agent leucocrystal violet under different preservation conditions including numbers 41-44 are as shown in Table 8.

TABLE 8

Changes of the absorbance of the color developing agent leucocrystal violet under different preservation conditions including numbers 41-44

| | Absorbance Number | | | |
|---|---|---|---|---|
| | 41 | 42 | 43 | 44 |
| | Preservation solution | | | |
| | 100 mM MES buffer with a pH of 5.00 | | | |
| Number of days | 3 mM sodium sulfite | 3 mM sodium thiosulfate | 3 mM sodium bisulfite | 3 mM 1-mercaptoglycerol |
| 0 day | 0.0096 | 0.0087 | 0.0086 | 0.0087 |
| 2nd day | 0.0287 | 0.0323 | 0.0322 | 0.0308 |
| 4th day | 0.0765 | 0.0855 | 0.0869 | 0.0887 |
| 6th day | 0.1127 | 0.1227 | 0.1248 | 0.1259 |
| 8th day | 0.1608 | 0.1706 | 0.1693 | 0.1736 |
| 10th day | 0.2100 | 0.2154 | 0.2183 | 0.2133 |
| 12th day | 0.2264 | 0.2422 | 0.2425 | 0.2488 |
| 14th day | 0.2372 | 0.2626 | 0.2623 | 0.2688 |
| Difference of the absorbance between the 14th day and the 0 day | 0.2276 | 0.2539 | 0.2537 | 0.2601 |

From Table 8, it can be seen that the color developing agent leucocrystal violet preserved in different reducing substance preservation solutions at 37° C. for 2 weeks has significant difference in absorbance. With the increase of preservation days, the absorbance of the color developing agent leucocrystal violet in an MES buffer which has a pH of 5 and contains 3 mM sodium sulfite is only increased by 0.2276, which is the smallest change in absorbance, and the buffer has a better effect of suppressing spontaneous color development than other reducing substances such as sodium thiosulfate, sodium bisulfite, and 1-mercaptoglycerol.

When the preservation solution is changed into other buffer solutions with a pH of 5, a preservation solution containing sodium sulfite also has a better effect of suppressing spontaneous color development than other reducing substances such as sodium thiosulfate, sodium bisulfite, and 1-mercaptoglycerol.

Example 9 Stability of Leucocrystal Violet Under Different Concentrations of Sodium Sulfite Preservation Conditions

1. Method

A color developing agent, namely leucocrystal violet, was dissolved in different concentrations of sodium sulfite preservation solutions separately, where the color developing agent leucocrystal violet had a final concentration of 10 μM. The solutions were preserved at 37° C. for 2 weeks. Parts of the solutions were extracted every 2 days. The absorbance at a wavelength of 590 nm was determined by an ultraviolet spectrophotometer.

2. Results

Changes of the absorbance of the color developing agent leucocrystal violet under different preservation conditions including numbers 45-48 are as shown in Table 9.

TABLE 9

Changes of the absorbance of the color developing agent leucocrystal violet under different preservation conditions including numbers 45-48

| | Absorbance Number | | | |
|---|---|---|---|---|
| | 45 | 46 | 47 | 48 |
| | Preservation solution | | | |
| | 100 mM MES buffer with a pH of 5.00 | | | |
| Number of days | 1 mM sodium sulfite | 5 mM sodium sulfite | 7 mM sodium sulfite | 10 mM sodium sulfite |
| 0 day | 0.0089 | 0.0092 | 0.0093 | 0.0087 |
| 2nd day | 0.0322 | 0.0248 | 0.022 | 0.0203 |
| 4th day | 0.0847 | 0.069 | 0.0649 | 0.0561 |
| 6th day | 0.1230 | 0.094 | 0.0909 | 0.0806 |
| 8th day | 0.1660 | 0.1359 | 0.1214 | 0.1094 |
| 10th day | 0.2218 | 0.167 | 0.1652 | 0.1449 |
| 12th day | 0.2390 | 0.1868 | 0.1747 | 0.1588 |
| 14th day | 0.2640 | 0.2088 | 0.1885 | 0.1775 |
| Difference of the absorbance between the 14th day and the 0 day | 0.2551 | 0.1996 | 0.1792 | 0.1688 |

From Table 9, it can be seen that the color developing agent leucocrystal violet preserved in different concentrations of sodium sulfite preservation solutions at 37° C. for 2 weeks has significant difference in absorbance. With the increase of preservation days, the absorbance of the color developing agent leucocrystal violet in an MES buffer with a number of 39 which has a pH of 5 and contains 10 mM sodium sulfite is only increased by 0.1688, which is the smallest change in absorbance, and the buffer has an optimal effect of suppressing spontaneous color development. It can be seen that when the leucocrystal violet is preserved in the MES buffer which has a pH of 5 and contains 10 mM sodium sulfite, an optimal stabilizing effect is achieved.

When the preservation solution is changed into other buffer solutions with a pH of 5, a buffer containing 10 mM sodium sulfite also has an optimal effect of stabilizing the leucocrystal violet.

Comparative Example Stability of DA-67 Under Different Preservation Conditions

1. Method

A color developing agent, namely sodium 10-(carboxymethylaminocarbonyl)-3,7-bis(dimethylamino)phenothiazine (DA-67), was dissolved in different preservation solutions separately, where the color developing agent DA-67 had a final concentration of 40 μM. The solutions were preserved at 37° C. for 2 weeks. Parts of the solutions were extracted every 2 days. The absorbance at a wavelength of 660 nm was determined by an ultraviolet spectrophotometer.

2. Results

Changes of the absorbance of the color developing agent DA-67 under different preservation conditions including numbers 49-52 are as shown in Table 10.

TABLE 10

Changes of the absorbance of the color developing agent DA-67 under different preservation conditions including numbers 49-52

| | Absorbance Number | | | |
|---|---|---|---|---|
| | 49 | 50 | 51 | 52 |
| | Preservation solution | | | |
| | 100 mM MES buffer with a pH of 5.00 | | | |
| Number of days | 3 mM 1-mercaptoglycerol | 3 mM sodium thiosulfate | 3 mM cetyltrimethylammonium bromide | 3 mM benzalkonium chloride |
| 0 day | 0.0233 | 0.0225 | 0.0234 | 0.0227 |
| 2nd day | 0.1214 | 0.1189 | 0.2018 | 0.1982 |
| 4th day | 0.2156 | 0.1905 | 0.3811 | 0.3605 |
| 6th day | 0.3044 | 0.2814 | 0.5436 | 0.5214 |
| 8th day | 0.3956 | 0.3762 | 0.7325 | 0.7157 |

TABLE 10-continued

Changes of the absorbance of the color developing agent DA-67 under different preservation conditions including numbers 49-52

| | Absorbance Number | | | |
|---|---|---|---|---|
| | 49 | 50 | 51 | 52 |
| | Preservation solution | | | |
| | 100 mM MES buffer with a pH of 5.00 | | | |
| Number of days | 3 mM 1-mercaptoglycerol | 3 mM sodium thiosulfate | 3 mM cetyltrimethylammonium bromide | 3 mM benzalkonium chloride |
| 10th day | 0.4836 | 0.4725 | 0.9117 | 0.8981 |
| 12th day | 0.6018 | 0.5714 | 1.0210 | 0.9892 |
| 14th day | 0.7014 | 0.6755 | 1.2658 | 1.1890 |
| Difference of the absorbance between the 14th day and the 0 day | 0.6781 | 0.653 | 1.2424 | 1.1663 |

From Table 10, it can be seen that the color developing agent DA-67 preserved in different preservation solutions at 37° C. for 2 weeks has significant difference in absorbance. The absorbance of the color developing agent DA-67 in preservation solutions containing cetyltrimethylammonium bromide and benzalkonium chloride is increased by 1.2424 and 1.1663 respectively, which is significantly higher than that in preservation solutions containing reducing substances such as 1-mercaptoglycerol and sodium thiosulfate. It is indicated that spontaneous color development of the color developing agent DA-67 in slightly acidic buffers containing the reducing substances such as 1-mercaptoglycerol and sodium thiosulfate is significantly lower than that in slightly acidic buffers containing quaternary ammonium salts, and the slightly acidic buffer preservation solutions containing the reducing substances such as 1-mercaptoglycerol and sodium thiosulfate has a better effect of stabilizing the color developing agent.

Application Example 1 Application of a Color Developing Agent

1. Method

A color developing agent was preserved in a weakly acidic buffer preservation solution containing a reducing substance, and used for determining glycosylated hemoglobin.

The reagent for determining the glycosylated hemoglobin includes the following components as shown in Table 11.

TABLE 11

Components of the reagent for determining the glycosylated hemoglobin

| | Component | Concentration |
|---|---|---|
| Pre-treatment solution | Triton X-100 | 2 g/L |
| | Sodium nitrite | 3 mM |
| Reagent R1 | Tris-HCl buffer | 100 mM, pH = 7.00 |
| | Peroxidase | 20 KU/L |
| | Fructosyl-amino acid oxidase | 10 KU/L |
| | Sodium azide | 2 g/L |

TABLE 11-continued

Components of the reagent for determining the glycosylated hemoglobin

| | Component | Concentration |
|---|---|---|
| Reagent R2 | MES buffer | 100 mM, pH = 6.00 |
| | DA-67 | 120 μM |
| | Sodium thiosulfate | 3 mM |
| | Proclin-300 | 0.03% |

A method for determining the glycosylated hemoglobin is as follows.

An anticoagulant, namely disodium EDTA, was added to a whole blood sample for centrifugation and layering. 25 μL red blood cells were taken from the lowest layer, and thoroughly mixed with 500 μL the pre-treatment solution to obtain a pre-treatment sample. 12 μL the pre-treatment sample was uniformly mixed with 180 μL the reagent R1 for incubation at 37° C. for 5 minutes, and an absorbance A1 at a wavelength of 660 nm was determined. Then, 60 μL the reagent R2 was added for uniform mixing and incubation at 37° C. for 5 minutes, and an absorbance A2 at a wavelength of 660 nm was determined. A difference of the A2 and the A1 was calculated.

Based on the above operation method and machine parameters, an automatic Hitachi 7180 biochemical analyzer was used for calibration. A linear relationship between the concentration of the glycosylated hemoglobin and the difference of the A2 and the A1 was determined. The concentration of the glycosylated hemoglobin was calculated based on the linear relationship between the glycosylated hemoglobin and the difference of the A2 and the A1 as well as the difference of the A2 and the A1 of the whole blood sample containing disodium EDTA.

After a stabilizer containing a reducing agent and the color developing agent were preserved together for a week, sodium thiosulfate was used as a reducing substance in the reagent R2 of Test 1. Vitamin C was used as a reducing substance in the reagent R2 of Test 2. Sodium borohydride was used as a reducing substance in the reagent R2 of Test 3. A kit for detecting glycosylated hemoglobin by an enzymatic method purchased from Sekisui Medical Technology (China) Co., Ltd. was used in Comparative Test 1, and Comparative Test 1 was carried out according to an instruction of the kit. The concentration of the glycosylated hemoglobin in 30 whole blood samples containing disodium EDTA was separately determined by using the reagents in Tests 1-3 and Comparative Test 1.

Figure 1:
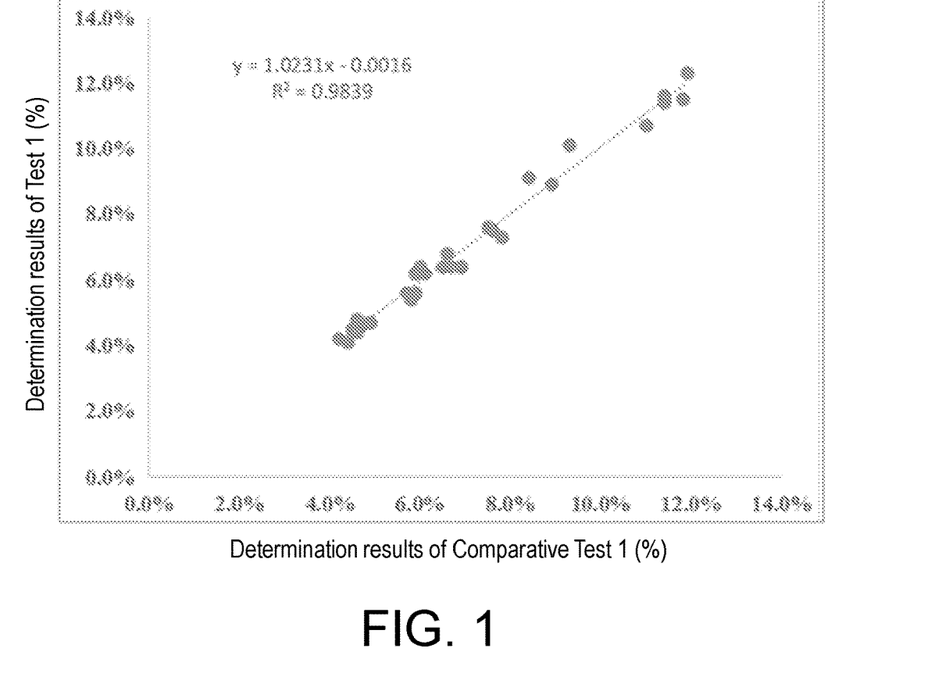
FIG. 1 is a diagram showing a correlation regression equation fitted with determination results of Comparative Test 1 as an X axis and determination results of Test 1 as a Y axis in the present invention.
Figure 2:
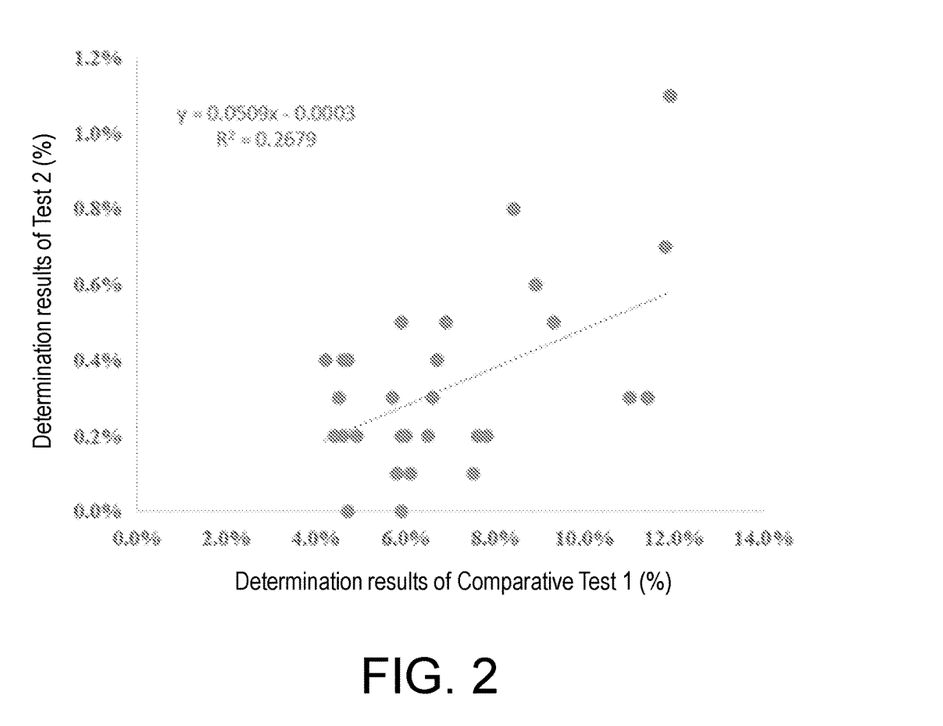
FIG. 2 is a diagram showing a correlation regression equation fitted with determination results of Comparative Test 1 as an X axis and determination results of Test 2 as a Y axis in the present invention.
Figure 3:
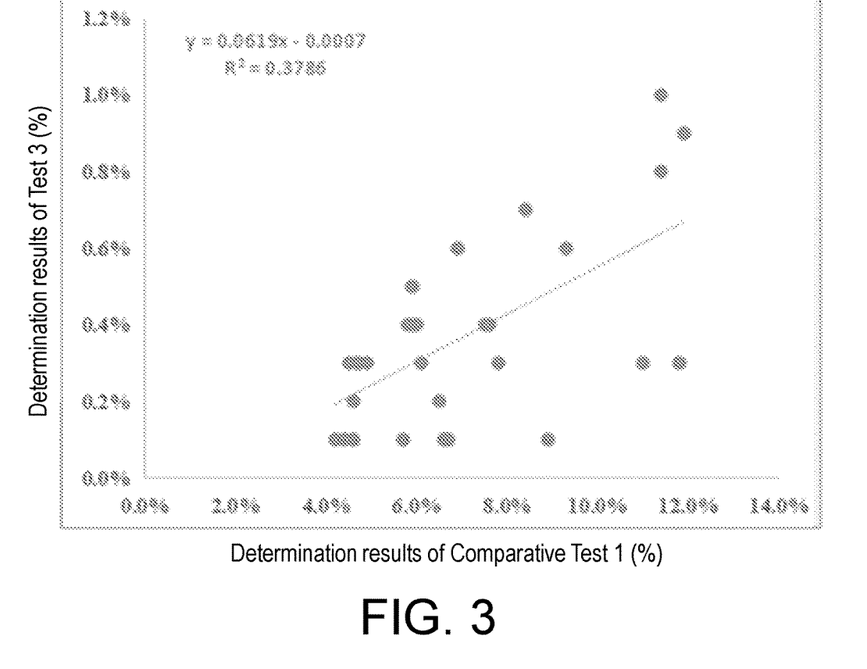
FIG. 3 is a diagram showing a correlation regression equation fitted with determination results of Comparative Test 1 as an X axis and determination results of Test 3 as a Y axis in the present invention.

Correlation regression equations were fitted with determination results of Comparative Test 1 as an X axis and determination results of Tests 1-3 as a Y axis respectively, and the influence of different reducing substances in the reagent R2 on the determination results was determined.

2. Results (1) Determination Results of the Concentration of the Glycosylated Hemoglobin in 30 Whole Blood Samples Containing Disodium EDTA The determination results of the concentration of the glycosylated hemoglobin in 30 whole blood samples containing disodium EDTA in Tests 1-3 and Comparative Test 1 are as shown in Table 12.

TABLE 12

Determination results of the concentration of the glycosylated hemoglobin in 30 whole blood samples containing disodium EDTA

| Serial number | Test 1 | Test 2 | Test 3 | Comparative Test 1 |
|---|---|---|---|---|
| 1 | 6.2% | 0.0% | 0.4% | 5.9% |
| 2 | 6.4% | 0.2% | 0.2% | 6.5% |
| 3 | 8.9% | 0.6% | 0.1% | 8.9% |
| 4 | 7.6% | 0.1% | 0.4% | 7.5% |
| 5 | 6.4% | 0.5% | 0.6% | 6.9% |
| 6 | 6.2% | 0.5% | 0.5% | 5.9% |
| 7 | 10.7% | 0.3% | 0.3% | 11.0% |
| 8 | 11.6% | 0.3% | 0.8% | 11.4% |
| 9 | 4.5% | 0.3% | 0.3% | 4.5% |
| 10 | 4.6% | 0.0% | 0.3% | 4.7% |
| 11 | 4.7% | 0.2% | 0.3% | 4.9% |
| 12 | 4.8% | 0.4% | 0.2% | 4.6% |
| 13 | 4.7% | 0.4% | 0.3% | 4.7% |
| 14 | 7.5% | 0.2% | 0.4% | 7.6% |
| 15 | 5.4% | 0.1% | 0.4% | 5.8% |
| 16 | 6.8% | 0.3% | 0.1% | 6.6% |
| 17 | 11.4% | 0.3% | 1.0% | 11.4% |
| 18 | 6.4% | 0.2% | 0.4% | 6.0% |
| 19 | 4.2% | 0.4% | 0.1% | 4.2% |
| 20 | 10.1% | 0.5% | 0.6% | 9.3% |
| 21 | 4.4% | 0.2% | 0.1% | 4.6% |
| 22 | 12.3% | 1.1% | 0.9% | 11.9% |
| 23 | 7.3% | 0.2% | 0.3% | 7.8% |
| 24 | 5.6% | 0.3% | 0.1% | 5.7% |
| 25 | 11.5% | 0.7% | 0.3% | 11.8% |
| 26 | 4.1% | 0.2% | 0.1% | 4.4% |
| 27 | 6.4% | 0.4% | 0.1% | 6.7% |
| 28 | 5.6% | 0.2% | 0.5% | 5.9% |
| 29 | 9.1% | 0.8% | 0.7% | 8.4% |
| 30 | 6.2% | 0.1% | 0.3% | 6.1% |

(2) Correlation Between the Determination Results of Tests 1-3 and the Determination Results of Comparative Test 1

Correlation regression equation diagrams were fitted with the determination results of Comparative Test 1 as an X axis and the determination results of Tests 1-3 as a Y axis respectively. Fitting correlation results of Tests 1-3 are as shown in FIG. 1 to FIG. 3 respectively. From FIG. 1, it can be seen that the fitting between the determination results of Test 1 and Comparative Test 1 has a good correlation with a correlation coefficient $R^2$ of 0.9839. However, from FIG. 2 and FIG. 3, it is shown that the fitting between the determination results of Tests 2-3 and Comparative Test 1 has a poor correlation with a correlation coefficient $R^2$ of 0.2679/0.3786. It is indicated that when vitamin C or sodium borohydride is used as the reducing substance in the reagent R2 of the kit, determination of the glycosylated hemoglobin is suppressed, and the determination accuracy is low. However, as claimed by the present invention, when, sodium thiosulfate is used as the reducing substance in the reagent R2 of the kit, no suppression reaction exists, the determination results have a good correlation with a commercial reagent, and the determination accuracy is high.

Application Example 2 Application of a Color Developing Agent

1. Method

A color developing agent was preserved in a weakly acidic buffer preservation solution containing a reducing substance, and used for determining a free fatty acid.

The reagent for determining the free fatty acid includes the following components as shown in Table 13.

TABLE 13

Components of the reagent for determining the free fatty acid

| Reagent type | Component | Concentration |
|---|---|---|
| Reagent R1 | HEPES buffer | 100 mM, pH = 7.50 |
| | Acyl-coenzyme A synthase | 120 μM |
| | Acyl-coenzyme A oxidase | 3 mM |
| | ATP | 6 mM |
| | Peroxidase | 0.03% |
| | Sodium azide | 0.8 g/L |
| Reagent R2 | Citric acid buffer | 50 mM, pH = 4.00 |
| | TergitolTM 15-S-9 | 2 g/L |
| | Coenzyme A | 0.3 mM |
| | Leucomalachite green | 30 μM |
| | Sodium sulfite | 2 mM |
| | Sodium benzoate | 6 mM |

A method for determining the free fatty acid is as follows.

3 μL serum was uniformly mixed with 180 μL the reagent R2 for incubation at 37° C. for 5 minutes, and an absorbance A1 at a wavelength of 600 nm was determined. Then, 45 μL the reagent R1 was added for uniform mixing and incubation at 37° C. for 5 minutes, and an absorbance A2 at a wavelength of 600 nm was determined. A difference of the A2 and the A1 was calculated.

Based on the above operation method and machine parameters, an automatic Hitachi 7180 biochemical analyzer was used for calibration. A linear relationship between the concentration of the free fatty acid and the difference of the A2 and the A1 was determined. The concentration of the free fatty acid was calculated based on the linear relationship between the free fatty acid and the difference of the A2 and the A1 as well as the difference of the A2 and the A1 of the serum sample.

After a stabilizer containing a reducing agent and the color developing agent were preserved together for a week, sodium sulfite was used as a reducing substance in the reagent R2 in Test 4. Vitamin C was used as a reducing substance in the reagent R2 in Test 5. Sodium borohydride was used as a reducing substance in the reagent R2 in Test 6. A kit for determining a free fatty acid purchased from DiaSys Diagnostic Systems (Shanghai) Co., Ltd. was used in Comparative Test 2, and Comparative Test 2 was carried out according to an instruction of the kit. The free fatty acid in 40 serum samples was separately determined by using the reagents in Tests 4-6 and Comparative Test 2.

Figure 4:
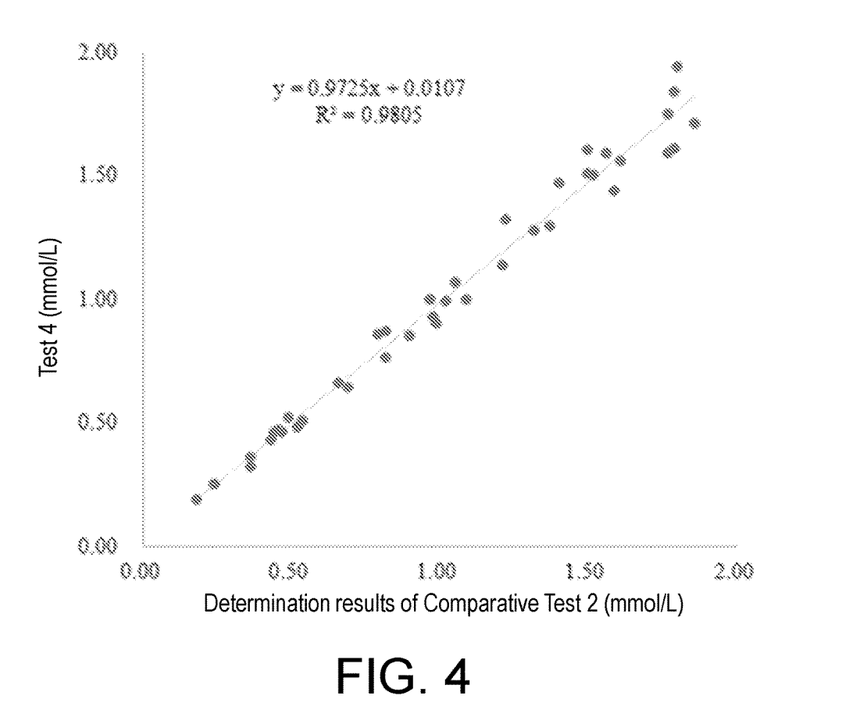
FIG. 4 is a diagram showing a correlation regression equation fitted with determination results of Comparative Test 2 as an X axis and determination results of Test 4 as a Y axis in the present invention.
Figure 5:
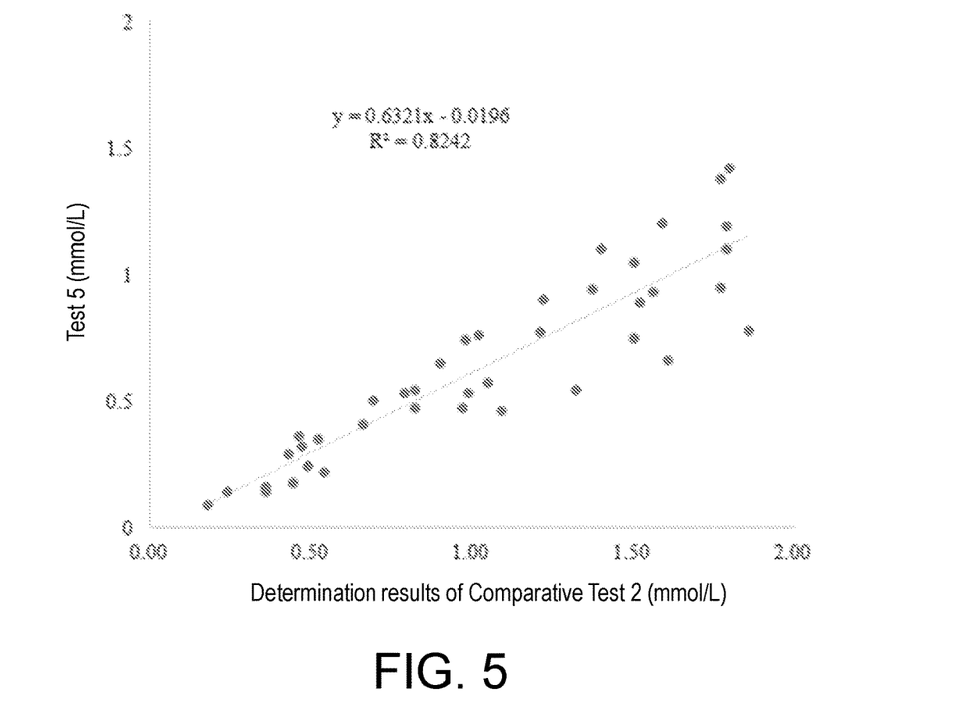
FIG. 5 is a diagram showing a correlation regression equation fitted with determination results of Comparative Test 2 as an X axis and determination results of Test 5 as a Y axis in the present invention.
Figure 6:
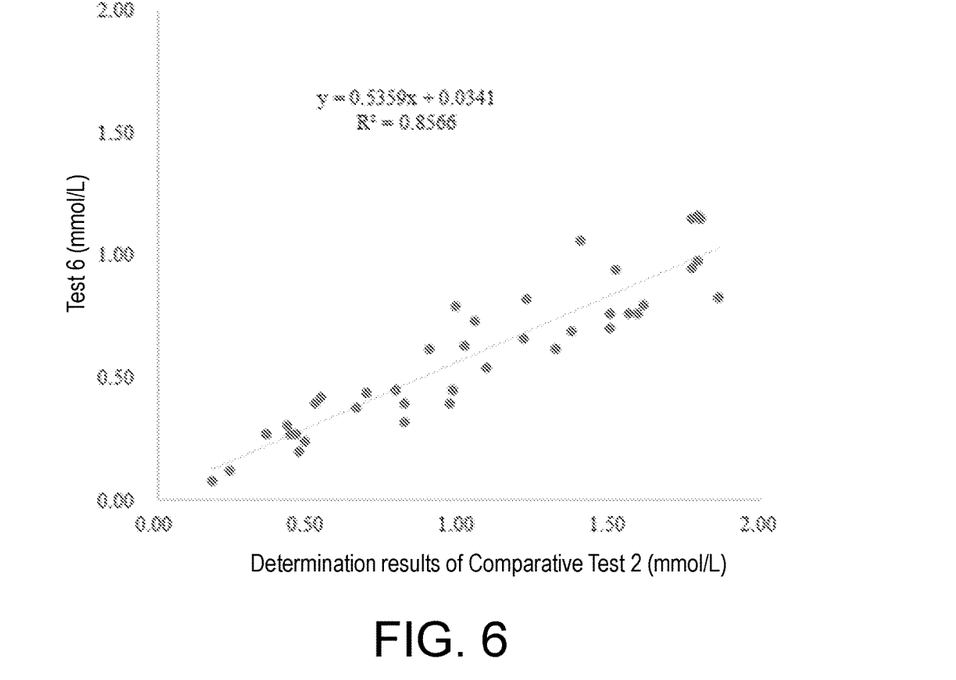
FIG. 6 is a diagram showing a correlation regression equation fitted with determination results of Comparative Test 2 as an X axis and determination results of Test 6 as a Y axis in the present invention.

Correlation regression equations were fitted with determination results of Comparative Test 2 as an X axis and determination results of Tests 4-6 as a Y axis respectively, and the influence of different reducing substances in the reagent R2 on the determination results was determined.

2. Results
(1) Determination Results of the Concentration of the Free Fatty Acid in 40 Serum Samples The determination results of the concentration of the free fatty acid in 40 serum samples in Tests 4-6 and Comparative Test 2 are as shown in Table 14.

TABLE 14

Determination results of the concentration of the free fatty acid in 40 serum samples

| Serial number | Comparative Test 2 | Test 4 | Test 5 | Test 6 |
|---|---|---|---|---|
| 1 | 1.02 | 0.99 | 0.76 | 0.63 |
| 2 | 1.80 | 1.94 | 1.42 | 1.15 |
| 3 | 1.50 | 1.60 | 0.75 | 0.76 |
| 4 | 0.24 | 0.25 | 0.14 | 0.12 |
| 5 | 0.66 | 0.66 | 0.41 | 0.38 |
| 6 | 1.79 | 1.84 | 1.10 | 0.98 |
| 7 | 1.22 | 1.32 | 0.90 | 0.82 |
| 8 | 1.21 | 1.14 | 0.77 | 0.66 |
| 9 | 0.99 | 0.90 | 0.53 | 0.79 |
| 10 | 1.79 | 1.61 | 1.19 | 1.16 |
| 11 | 0.54 | 0.51 | 0.22 | 0.42 |
| 12 | 1.37 | 1.30 | 0.94 | 0.69 |
| 13 | 1.56 | 1.59 | 0.93 | 0.76 |
| 14 | 0.36 | 0.36 | 0.16 | 0.27 |
| 15 | 1.05 | 1.07 | 0.57 | 0.73 |
| 16 | 1.77 | 1.75 | 1.38 | 1.15 |
| 17 | 0.82 | 0.87 | 0.47 | 0.32 |
| 18 | 1.77 | 1.59 | 0.95 | 0.95 |
| 19 | 0.52 | 0.48 | 0.35 | 0.40 |
| 20 | 1.52 | 1.50 | 0.89 | 0.94 |
| 21 | 0.44 | 0.46 | 0.18 | 0.27 |
| 22 | 1.40 | 1.47 | 1.10 | 1.06 |
| 23 | 0.18 | 0.19 | 0.09 | 0.08 |
| 24 | 0.98 | 0.93 | 0.74 | 0.45 |
| 25 | 0.79 | 0.86 | 0.53 | 0.45 |
| 26 | 0.36 | 0.32 | 0.14 | 0.27 |
| 27 | 1.09 | 1.00 | 0.46 | 0.54 |
| 28 | 1.59 | 1.44 | 1.20 | 0.76 |
| 29 | 0.47 | 0.46 | 0.32 | 0.20 |
| 30 | 0.90 | 0.85 | 0.65 | 0.62 |
| 31 | 0.46 | 0.47 | 0.36 | 0.27 |
| 32 | 1.86 | 1.71 | 0.78 | 0.83 |
| 33 | 1.32 | 1.28 | 0.54 | 0.62 |
| 34 | 0.43 | 0.43 | 0.29 | 0.31 |
| 35 | 0.97 | 1.00 | 0.47 | 0.40 |
| 36 | 1.50 | 1.51 | 1.05 | 0.70 |
| 37 | 0.82 | 0.76 | 0.54 | 0.40 |
| 38 | 0.49 | 0.52 | 0.24 | 0.24 |
| 39 | 1.61 | 1.56 | 0.66 | 0.80 |
| 40 | 0.69 | 0.64 | 0.50 | 0.44 |

(2) Correlation Between the Determination Results of Tests 4-6 and the Determination Results of Comparative Test 2

Correlation regression equation diagrams were fitted with the determination results of Comparative Test 2 as an X axis and the determination results of Tests 4-6 as a Y axis respectively. Fitting correlation results of Tests 4-6 are as shown in FIG. 4 to FIG. 6 respectively. From FIG. 4, it can be seen that the fitting between the determination results of Test 4 and Comparative Test 2 has a good correlation with a correlation coefficient $R^2$ of 0.9805. However, from FIG. 5 and FIG. 6, it is shown that the fitting between the determination results of Tests 5-6 and Comparative Test 2 has a poor correlation with a correlation coefficient $R^2$ of 0.8242/0.8566. It is indicated that when vitamin C or sodium borohydride is used as the reducing substance in the reagent R2 of the kit, determination of the free fatty acid is suppressed, and the determination accuracy is low. However, as claimed by the present invention, when sodium sulfite is used as the reducing substance in the reagent R2 of the kit, no suppression reaction exists, the determination results have a good correlation with a commercial reagent, and the determination accuracy is high.

The above examples are preferable embodiments of the present invention, but the embodiments of the present invention are not limited by the above embodiments. Any other changes, modifications, substitutions, combinations, and simplifications made without departing from the spirit essence and principle of the present invention shall be considered as equivalent substitutions, and shall be included in the protection scope of the present invention.

What is claimed is:

1. A kit, comprising a reagent R2, wherein the reagent R2 comprises a color developing agent and a stabilizer,
    wherein the stabilizer includes a reducing substance and a weakly acidic buffer having a pH of 3.8-6.2,
    wherein the stabilizer is used to preserve the color developing agent,
    wherein the reducing substance is sodium thiosulfate and has a concentration of 5-10 mM, the weakly acidic buffer is citric acid buffer, and the color developing agent is a phenothiazine color developing agent.

2. The kit according to claim 1, wherein the phenothiazine color developing agent comprises one or two of sodium 10-(carboxymethylaminocarbonyl)-3,7-bis(dimethylamino) phenothiazine or 3,7-bis(dimethylamino)-N-ethyl-10H-phenothiazine-10-formamide.

3. The kit according to claim 1, wherein the weakly acidic buffer has a pH of 4-6.

* * * * *